United States Patent
Jain et al.

(10) Patent No.: US 11,857,546 B2
(45) Date of Patent: Jan. 2, 2024

(54) CRENOLANIB FOR TREATING FLT3 MUTATED PROLIFERATIVE DISORDERS RELAPSED/REFRACTORY TO PRIOR TREATMENT

(71) Applicant: Arog Pharmaceuticals, Inc., Plano, TX (US)

(72) Inventors: Vinay K. Jain, Dallas, TX (US); Bothayna Messahel, Coppell, TX (US)

(73) Assignee: AROG PHARMACEUTICALS, INC., Plano, TX (US)

( * ) Notice: Subject to any disclaimer, the term of this patent is extended or adjusted under 35 U.S.C. 154(b) by 0 days.

(21) Appl. No.: 17/830,682

(22) Filed: Jun. 2, 2022

(65) Prior Publication Data
US 2023/0128591 A1    Apr. 27, 2023

Related U.S. Application Data

(60) Provisional application No. 63/270,887, filed on Oct. 22, 2021.

(51) Int. Cl.
*A61K 31/4709*    (2006.01)
*C12Q 1/6886*    (2018.01)
*A61P 35/02*    (2006.01)

(52) U.S. Cl.
CPC .......... *A61K 31/4709* (2013.01); *A61P 35/02* (2018.01); *C12Q 1/6886* (2013.01); *C12Q 2600/156* (2013.01)

(58) Field of Classification Search
CPC .................. A61K 9/0053; A61K 31/4709
See application file for complete search history.

(56) References Cited

U.S. PATENT DOCUMENTS

| | | | |
|---|---|---|---|
| 2,403,876 | A | 7/1946 | Nord |
| 5,990,146 | A | 11/1999 | Boschelli et al. |
| 7,183,414 | B2 | 2/2007 | Tom et al. |
| 10,213,423 | B2 * | 2/2019 | Jain ............... A61K 9/0053 |
| 2005/0124599 | A1 | 6/2005 | Kath et al. |
| 2021/0324481 | A1 | 10/2021 | Jain |

FOREIGN PATENT DOCUMENTS

| | | |
|---|---|---|
| WO | 9916755 A1 | 4/1999 |
| WO | 0140217 A1 | 6/2001 |

OTHER PUBLICATIONS

Pinedo et al. (2000).*
McMahon et al. (2000).*
United States Patent & Trademark Office (ISA), International Search Report and Written Opinion for PCT/US22/31912 dated Sep. 13, 2022, 10 pp.
Altman, et al. "The impact of FLT3 mutation clearance and treatment response after gilteritinib therapy on overall survival in patients with FLT3 mutation-positive relapsed/refractory acute myeloid leukemia" (2012). Cancer Med, 10(3), 797-805. doi:10.1002/cam4.3652.
Amin, et al. "Having a higher blast percentage in circulation than bone marrow: clinical implications in myelodysplastic syndrome and acute lymphoid and myeloid leukemias" (2005). Leukemia, 19(9), 1567-1572. doi:10.1038/sj.leu.2403876.
Bejanyan, et al. "Survival of patients with acute myeloid leukemia relapsing after allogeneic hematopoietic cell transplantation: a center for international blood and marrow transplant research study" (2015). Biol Blood Marrow Transplant, 21(3), 454-459. doi:10.1016/j.bbmt.2014.11.007.
Borthakur, et al. "Phase I study of sorafenib in patients with refractory or relapsed acute leukemias" (2011). Haematologica, 96(1), 62-68. doi:10.3324/haematol.2010.030452.
Cheson, et al. "Reporting Standards for Therapeutic Trials in Acute Myeloid" (2003). Revised recommendations of the International Working Group for Diagnosis, Standardization of Response Criteria, Treatment Outcomes, and Reporting Standards for Therapeutic Trials in Acute Myeloid Leukemia. J Clin Oncol, 21(24), 4642-4649. doi:10.1200/JCO.2003.04.036.
Stone, et al. "Patients with acute myeloid leukemia and an activating mutation in FLT3 respond to a small-molecule FLT3 tyrosine kinase inhibitor, PKC412" (2005). Blood, 105(1), 54-60. doi:10.1182/blood-2004-03-0891.
Dohner, et al. "Diagnosis and management of AML in adults: 2017 ELN recommendations from an international expert panel" (2017). Blood, 129(4), 424-447. doi:10.1182/blood-2016-08-733196.
FDA "Gilteritinib FDA SUPPL-1" (2019) Retrieved from https://www.accessdata.fda.gov/drugsatfda_docs/label/2019/211349s001lbl.pdf.
FDA "Rydapt FDA Label Suppl-4 (Mar. 2020)" (2020) Retrieved from https://www.accessdata.fda.gov/drugsatfda_docs/label/2020/207997s004lbl.pdf.
Gilliland, et al. "The roles of FLT3 in hematopoiesis and leukemia" (2002). Blood, 100(5), 1532-1542. doi:10.1182/blood-2002-02-0492.
Griswold, et al. "Effects of MLN518, a dual FLT3 and KIT inhibitor, on normal and malignant hematopoiesis" (2004). Blood, 104(9), 2912-2918. doi:10.1182/blood-2003-05-1669.
Joshi, et al. "A noncanonical FLT3 gatekeeper mutation disrupts gilteritinib binding and confers resistance" (2021). Am J Hematol, 96(7), E226-E229. doi:10.1002/ajh.26174.
Levis, et al. "A FLT3-targeted tyrosine kinase inhibitor is cytotoxic to leukemia cells in vitro and in vivo" (2002). Blood, 99(11), 3885-3891. Retrieved from https://www.ncbi.nlm.nih.gov/pubmed/12010785.

(Continued)

*Primary Examiner* — Paul V Ward
(74) *Attorney, Agent, or Firm* — Edwin S. Flores; Daniel J. Chalker; Chalker Flores, LLP

(57) ABSTRACT

The present invention includes methods for treating a proliferative disorder in a subject with mutated or constitutively active FLT3 in a subject relapsed/refractory to one or more prior tyrosine kinase inhibitors comprising: obtaining a tumor sample from the subject that is relapsed/refractory to one or more prior tyrosine kinase inhibitors; measuring expression of mutated or constitutively active FLT3 mutant in the tumor sample; and administering to the subject a therapeutically effective amount of crenolanib or a pharmaceutically acceptable salt thereof sufficient to treat the proliferative disorder.

9 Claims, No Drawings

(56) References Cited

OTHER PUBLICATIONS

Levis, et al. "Small molecule FLT3 tyrosine kinase inhibitors" (2004). Curr Pharm Des, 10(11), 1183-1193. doi:10.2174/1381612043452604.

Lewis, et al. "Phase I study of the safety, tolerability, and pharmacokinetics of oral CP-868,596, a highly specific platelet-derived growth factor receptor tyrosine kinase inhibitor in patients with advanced cancers" (2009). J Clin Oncol, 27(31), 5262-5269. doi:10.1200/JCO.2009.21.8487.

Majothi, et al. "FLT3 inhibitors in acute myeloid leukaemia: assessment of clinical effectiveness, adverse events and future research-a systematic review and meta-analysis" (2020). Syst Rev, 9(1), 285. doi:10.1186/s13643-020-01540-1.

McMahon, et al. "Clonal selection with Ras pathway activation mediates secondary clinical resistance to selective FLT3 inhibition in acute myeloid leukemia" (2019). Cancer Discov. doi: 10.1158/2159-8290.CD-18-1453.

Murata, et al. "Selective cytotoxic mechanism of GTP-14564, a novel tyrosine kinase inhibitor in leukemia cells expressing a constitutively active Fms-like tyrosine kinase 3 (FLT3)" (2003). J Biol Chem, 278(35), 32892-32898. doi:10.1074/jbc.M210405200.

O'Farrell, et al. "SU11248 is a novel FLT3 tyrosine kinase inhibitor with potent activity in vitro and in vivo" (2003) Blood, 101(9), 3597-3605. doi: 10.1182/blood-2002-07-2307.

Papaemmanuil, et al. "Genomic Classification and Prognosis in Acute Myeloid Leukemia" (2016). N Engl J Med, 374(23), 2209-2221. doi:10.1056/NEJMoa1516192.

Perl, et al. "AML-091: Clinical Outcomes in Patients with Relapsed/Refractory Acute Myeloid Leukemia Treated with Gilteritinib Who Received Prior Midostaurin or Sorafenib" (2021). Clinical Lymphoma Myeloma and Leukemia, 21, S280. doi:https://doi.org/10.1016/S2152-2650(21)01674-8.

Perl, et al. "Gilteritinib or Chemotherapy for Relapsed or Refractory FLT3-Mutated AML" (2019). New England Journal of Medicine, 381(18), 1728-1740. doi:10.1056/NEJMoa1902688.

Rucker, et al. "Molecular landscape and prognostic impact of FLT3-ITD insertion site in acute myeloid leukemia: RATIFY study results" (2021). Leukemia. doi:10.1038/s41375-021-01323-0.

Tyner, et al. "Functional genomic landscape of acute myeloid leukemia" (2018) Nature. doi:10.1038/s41586-018-0623-z.

Schmalbrock, et al. "Clonal evolution of acute myeloid leukemia with FLT3-ITD mutation under treatment with midostaurin" (2021) Blood. doi:10.1182/blood.2020007626.

Small, D. "FLT3 mutations: biology and treatment" (2006) Hematology Am Soc Hematol Educ Program, 178-184. doi:10.1182/asheducation-2006.1.178.

Smith, et al. "Single-agent CEP-701, a novel FLT3 inhibitor, shows biologic and clinical activity in patients with relapsed or refractory acute myeloid leukemia" (2004). Blood, 103(10), 3669-3676. doi:10.1182/blood-2003-11-3775.

Smith, et al. "Crenolanib is a selective type I pan-FLT3 inhibitor" (2014). Proc Natl Acad Sci U S A, 111(14), 5319-5324. doi:10.1073/pnas.1320661111.

Smith, et al. " FLT3 D835 mutations confer differential resistance to type II FLT3 inhibitors" (2015) Leukemia, 29(12), 2390-2392. doi:10.1038/leu.2015.165.

Yee, et al. "SU5416 and SU5614 inhibit kinase activity of wild-type and mutant FLT3 receptor tyrosine kinase" (2002) . Blood, 100(8), 2941-2949. doi:10.1182/blood-2002-02-0531.

\* cited by examiner

CRENOLANIB FOR TREATING FLT3 MUTATED PROLIFERATIVE DISORDERS RELAPSED/REFRACTORY TO PRIOR TREATMENT

CROSS-REFERENCE TO RELATED APPLICATIONS

This application claims priority to U.S. Provisional Application Ser. No. 63/270,887, filed Oct. 22, 2021, the entire contents of which is incorporated herein by reference.

TECHNICAL FIELD OF THE INVENTION

The present invention is directed to the use of crenolanib, or salts thereof, as a single agent or in combination with another pharmaceutical agent for the treatment of cancer, and to methods for treating animals suffering from FLT3 mutated proliferative disorders that are relapsed/refractory to a prior cancer treatment.

STATEMENT OF FEDERALLY FUNDED RESEARCH

Not applicable.

INCORPORATION-BY-REFERENCE OF MATERIALS FILED ON COMPACT DISK

Not applicable.

BACKGROUND OF THE INVENTION

Without limiting the scope of the invention, its background is described in connection with its ability to inhibit FLT3 tyrosine kinase in the treatment of proliferative disorders involving mutated or otherwise activated FLT3.

Protein kinases are enzymes that chemically modify other proteins by catalyzing the transfer of a phosphate group to amino acid residues serine, threonine, or tyrosine. Approximately 30% of all human proteins may be modified by kinase activity and kinase signaling is involved in a number of cellular processes including growth, proliferation, and survival.

Due to their involvement in cell proliferation and survival, aberrant expression, or activation of protein kinases, including through mutations, copy number gain, amplification, gene fusion, or other mechanisms are frequently associated with proliferative diseases including various cancers. Thus, investigating compounds that potently inhibit the activity and function of protein kinases will allow for a greater understanding of the physiological roles of protein kinases.

The FMS-like tyrosine kinase 3 (FLT3) gene encodes a membrane bound receptor tyrosine kinase that affects hematopoiesis, and aberrations in FLT3 signaling can lead to hematological disorders and malignancies. (Gilliland & Griffin, 2002; Stirewalt & Radich, 2003). Activation of the FLT3 receptor tyrosine kinase is initiated through the binding of the FLT3 ligand (FLT3L) to the FLT3 receptor, which initiates homodimerization of the ligand bound receptor, cross-phosphorylation, and recruitment of downstream signaling factors.

FLT3 is one of the most frequently mutated genes in hematological malignancies, present in approximately 30% of adult acute myeloid leukemias (AML). (Papaemmanuil et al., 2016; Rucker et al., 2021; Tyner et al., 2018), and the presence or absence of FLT3 mutations are included in international guidelines on AML risk stratification. (Dohner et al., 2017).

The most common FLT3 mutations are internal tandem duplications (ITD) that lead to in-frame insertions within the juxtamembrane domain of the FLT3 receptor and have been reported in 20-30% of adult AML patients. FLT3-ITD mutations are an independent predictor of poor patient prognosis and are associated with increased risk of relapse after standard therapy as well as decreased disease-free and overall survival. (DiNardo & Lachowiez, 2019; Papaemmanuil et al., 2016; Rucker et al., 2021; Sakaguchi et al., 2019; Tyner et al., 2018). Point mutations with the ligand binding or kinase domain mutations are less frequent than ITD mutations, but are also prognostically significant. The most commonly affected amino acid residue is aspartate 835 (D835) in the activation loop. Missense mutations (nucleotide substitutions) at D835 occur in approximately 5-10% of adult AML patients. (Stirewalt & Radich, 2003; Tyner et al., 2018). While ITD and D835 mutations are detectable using a PCR based technique that allows for relatively quick results at relatively low cost, the current commercial availability of Next Generation Sequencing panels, and the more widespread availability of the reagents and machines necessary for such panels to be performed outside of commercial labs, has redefined the mutational landscape of AML in general and FLT3-mutant AML in particular. An in-depth genetic analysis of over 500 AML patient samples found that up to 20% of the identified point mutations in FLT3 did not involve amino acid D835. (Tyner et al., 2018).

The frequency of FLT3 activating mutations in AML has made this kinase an attractive target in drug development. Several FLT3 inhibitors with varying degrees of potency and selectivity for activated FLT3 have been or are currently being investigated in AML patients. To date, two FLT3 inhibitors have been approved by the United States Food and Drug Administration (FDA) or the European Medicines Agency (EMA) for use in FLT3 mutated AML: midostaurin is approved in combination with chemotherapy for the treatment of newly diagnosed FLT3 mutated AML; gilteritinib is approved for use as a single agent in relapsed or refractory FLT3-mutated AML. (FDA, 2019, 2020). While midostaurin and gilteritinib are the only currently approved FLT3 inhibitors, a number of other compounds have been investigated in the past or are currently being investigated.

While FLT3 inhibition has proven to be a desirable treatment option, there are some disadvantages to single agent targeted treatment. The majority of FLT3 inhibitors tested are tyrosine kinase inhibitors (TKIs), including midostaurin, gilteritinib, and the present invention. Tyrosine kinase inhibitors can be vulnerable to resistance mutations, that is mutations within the target gene that confer resistance to specific TKIs. Not only does the presence of a resistance conferring mutation before administration of a TKI predict a poor response, but patients may acquire resistance conferring mutations while receiving a TKI and relapse. Often these resistance conferring mutations cause a conformational change in the kinase that prevents binding of the TKI.

For example, canonical FLT3 kinase domain mutations at amino acid residue D835 confer resistance to the TKIs quizartinib and sorafenib. Quizartinib and sorafenib are both "type II" inhibitors, which bind to a hydrophobic site near the ATP binding pocket. Mutations at D835 alter the conformation of this hydrophobic site and prevent binding of the inhibitors. (C. C. Smith, Lin, Stecula, Sali, & Shah, 2015). Mutations at amino acid F691 and N701, the "gatekeeper residues", confer resistance to gilteritinib by altering the conformation of the ATP binding pocket where gilteritinib binds. (Joshi et al., 2021). Up to 12% of patients who relapse after single-agent gilteritinib therapy develop FLT3-F691 mutations that contribute to relapse. (McMahon et al., 2019). Mutations at amino acid residues A637, N676, G697, Y842, and A848 have also been associated with resistance to a number of FLT3 inhibitors. (Wang et al., 2021). The acquisition of secondary FLT3 mutations may explain the relatively short event-free survival (EFS) observed on single agent FLT3 inhibitors, with the median EFS on gilteritinib monotherapy reported as 2.8 months. (Perl et al., 2019).

The majority of patients treated with either midostaurin or gilteritinib remain FLT3 mutated at relapse, with either retention of the original mutated clone or acquisition of a secondary mutation. (Altman et al., 2021; McMahon et al., 2019; Schmalbrock et al., 2021). These patients would benefit from the administration of a FLT3 inhibitor at relapse, as salvage chemotherapy alone does not provide high cure rates for relapsed/refractory FLT3 mutant AML (see: control arm of the gilteritinib phase III trial). (Perl et al., 2019). However, due in part to the potential acquisition of resistance conferring mutations, patients who are relapsed/refractory to one FLT3 TKI are less likely to benefit from the single agent administration of a second, or even third, FLT3 TKI. (Perl et al., 2021).

For patients to receive the optimal benefit, the use of a pan-FLT3 inhibitor active against a number of resistance-conferring FLT3 mutants, alone or in combination with another pharmaceutical agent, is necessary. Thus, treating patients with FLT3 mutated proliferative disorders who have progressed on one or more FLT3 tyrosine kinase inhibitors remains an unmet need.

SUMMARY OF THE INVENTION

The current invention overcomes the limitations of the prior art by using crenolanib (and pharmaceutically acceptable salts thereof), a potent pan-FLT3 inhibitor with activity against resistance conferring mutations, in the treatment of FLT3 mutated proliferative disorders that are relapsed or refractory after prior FLT3 inhibitor treatment.

In one embodiment, the present invention includes a method of treating a proliferative disorder in a subject with mutated or constitutively active FLT3 in a subject relapsed/refractory to one or more prior tyrosine kinase inhibitors comprising: obtaining a tumor sample from the subject that is relapsed/refractory to one or more prior tyrosine kinase inhibitors; measuring expression of mutated or constitutively active FLT3 mutant in the tumor sample; and administering to the subject a therapeutically effective amount of crenolanib or a pharmaceutically acceptable salt thereof sufficient to treat the proliferative disorder. In one aspect, the mutated or constitutively active FLT3 is at least one of FLT3-ITD; FLT3-TKD; an activating mutation in FLT3; a copy number gain or amplification of the FLT3 gene; or a gene fusion comprising a fusion of FLT3 with another gene. In another aspect, the subject has been provided a prior tyrosine kinase inhibitor selected from midostaurin, sorafenib, gilteritinib, quizartinib, pexidartinib, FF-10101, CG-806, lestaurtinib, AG1295, AG1296, CEP-5214, CEP-7055, HM43239, pacritinib, MAX-40279, FYSYN, NMS-03592088, or TG02 citrate; or the subject has a FLT3 mutation that confers resistance to the prior tyrosine kinase inhibitor. In another aspect, the resistance-conferring FLT3 mutation is selected from a missense mutation occurring in at least one of amino acid residues K429, A627, N676, A680, F691, Y693, G697, D698, N701, D835, N841, Y842, A848 present alone, or in combination with a FLT3-ITD mutation. In another aspect, the resistance-conferring FLT3 mutation was present before administration of the prior tyrosine kinase inhibitor or wherein the resistance conferring FLT3 mutation was acquired during or after administration of the prior tyrosine kinase inhibitor. In another aspect, the proliferative disorder is selected from at least one of a gastrointestinal stromal tumor, leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the therapeutically effective amount of crenolanib or the pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day. In another aspect, the therapeutically effective amount of crenolanib or the pharmaceutically acceptable salt thereof is administered at least one of continuously, intermittently, systemically, or locally. In another aspect, the therapeutically effective amount of crenolanib or the pharmaceutically acceptable salt thereof is administered orally, intravenously, or intraperitoneally. In another aspect, the therapeutically effective amount of crenolanib or the pharmaceutically acceptable salt thereof is administered up to three times or more a day for as long as the subject is in need of treatment for the proliferative disorder. In another aspect, the therapeutically effective amount of crenolanib or the pharmaceutically acceptable salt thereof is: provided at least one of sequentially or concomitantly with another pharmaceutical agent to maintain remission of an existing patient; provided as a single agent or in combination with another pharmaceutical agent in a patient to maintain remission, or in a relapsed/refractory proliferative disorder patient; or provided as a single agent or in combination with another pharmaceutical agent to maintain remission, or in a relapsed/refractory proliferative disorder pediatric patient. In another aspect, the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, or crenolanib succinate.

In another embodiment, the present invention includes a method of inhibiting or reducing mutant FLT3 tyrosine kinase activity or expression in a subject suffering from a proliferative disorder comprising: identifying that the subject discontinued a prior tyrosine kinase inhibitor therapy due to refractory or relapsed proliferative disease; obtaining a tumor sample from the subject; measuring expression of a mutated FLT3 or a constitutively active FLT3 mutant in the tumor sample; and if the subject has the mutated FLT3 or constitutively active FLT3 mutant, administering to the subject a therapeutically effective amount of crenolanib or a pharmaceutically acceptable salt thereof, wherein the crenolanib or salt thereof reduces a proliferative disorder burden or prevents proliferative disease progression. In one aspect, the mutated or constitutively active FLT3 is at least one of FLT3-ITD; FLT3-TKD; an activating mutation in FLT3; a copy number gain or amplification of the FLT3 gene; or a gene fusion comprising a fusion of FLT3 with another gene. In another aspect, the subject has been provided a prior tyrosine kinase inhibitor selected from midostaurin, sorafenib, gilteritinib, quizartinib, pexidartinib, FF-10101, CG-806, lestaurtinib, AG1295, AG1296, CEP-5214, CEP-7055, HM43239, pacritinib, MAX-40279, FYSYN, NMS-03592088, or TG02 citrate; or the subject has a FLT3 mutation that confers resistance to the prior tyrosine kinase inhibitor. In another aspect, the subject is relapsed or refractory to the prior tyrosine inhibitor and wherein the subject has a resistance-conferring FLT3 mutation selected from a missense mutation occurring in at least one of amino acid residues K429, A627, N676, A680, F691, Y693, G697, D698, N701, D835, N841, Y842, A848 present alone, or in combination with a FLT3-ITD mutation. In another aspect, the resistance-conferring FLT3 mutation was present before administration of the prior tyrosine kinase inhibitor or wherein the resistance conferring FLT3 mutation was acquired during or after administration of the prior tyrosine kinase inhibitor. In another aspect, the proliferative disorder is selected from at least one of a gastrointestinal stromal tumor, leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the therapeutically effective amount of crenolanib or the pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day. In another aspect, the therapeutically effective amount of crenolanib or the pharmaceutically acceptable salt thereof is administered at least one of continuously, intermittently, systemically, or locally. In another aspect, the therapeutically effective amount of crenolanib or the pharmaceutically acceptable salt thereof is administered orally, intravenously, or intraperitoneally. In another aspect, the therapeutically effective amount of crenolanib or the pharmaceutically acceptable salt thereof is administered up to three times or more a day for as long as the subject is in need of treatment for the proliferative disorder. In another aspect, the therapeutically effective amount of crenolanib or the pharmaceutically acceptable salt thereof is: provided at least one of sequentially or concomitantly with another pharmaceutical agent to maintain remission of an existing patient; provided as a single agent or in combination with another pharmaceutical agent in a patient to maintain remission, or in a relapsed/refractory proliferative disorder patient; or provided as a single agent or in combination with another pharmaceutical agent to maintain remission, or in a relapsed/refractory proliferative disorder pediatric patient. In another aspect, the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, or crenolanib succinate.

In another embodiment, the present invention includes a method for treating a subject suffering from a proliferative disorder, the method comprising the steps of: determining whether the subject has increased FLT3 tyrosine kinase activity by: obtaining or having obtained a biological sample from the patient; and performing or having performed an assay on the biological sample to determine if the patient has a gene mutation in the FLT3 gene, a change in the kinase activity of the FLT3 tyrosine kinase, overexpression of the FLT3 tyrosine kinase, or a change in the phenotype or genotype of the FLT3 tyrosine kinase; treating the patient with a first tyrosine kinase inhibitor; and if the patient is refractory to or relapses after the first tyrosine kinase inhibitor, and the patient has a gene mutation in FLT3; a change in the kinase activity of FLT3, overexpression of FLT3, or a change in the phenotype or genotype of FLT3 tyrosine kinase, then discontinuing administration of the first tyrosine kinase inhibitor and internally administering crenolanib to the patient in an effective amount to reduce a proliferative disorder burden or to prevent proliferative disease progression. In one aspect, the mutated or constitutively active FLT3 is at least one of FLT3-ITD; FLT3-TKD; an activating mutation in FLT3; a copy number gain or an amplification of the FLT3 gene; or a gene fusion comprising the fusion of FLT3 with another gene. In another aspect, the subject has been provided a prior tyrosine kinase inhibitor selected from midostaurin, sorafenib, gilteritinib, quizartinib, pexidartinib FF-10101, CG-806, lestaurtinib, AG1295, AG1296, CEP-5214, CEP-7055, HM43239, pacritinib, MAX-40279, FYSYN, NMS-03592088, or TG02 citrate; or the subject has a FLT3 mutation that confers resistance to the prior tyrosine kinase inhibitor. In another aspect, the mutation in the FLT3 gene or change in phenotype or genotype of FLT3 is a resistance-conferring mutation selected from a missense mutation occurring in at least one of amino acid residues K429, A627, N676, A680, F691, Y693, G697, D698, N701, D835, N841, Y842, A848 present alone or in combination with a FLT3-ITD mutation. In another aspect, the resistance-conferring FLT3 mutation was present before administration of the prior tyrosine kinase inhibitor or wherein the resistance conferring FLT3 mutation was acquired during or after administration of the prior tyrosine kinase inhibitor. In another aspect, the proliferative disorder is selected from at least one of a gastrointestinal stromal tumor, leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the therapeutically effective amount of crenolanib or the pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day. In another aspect, the therapeutically effective amount of crenolanib or the pharmaceutically acceptable salt thereof is administered at least one of continuously, intermittently, systemically, or locally. In another aspect, the therapeutically effective amount of crenolanib or the pharmaceutically acceptable salt thereof is administered orally, intravenously, or intraperitoneally. In another aspect, the therapeutically effective amount of crenolanib or the pharmaceutically acceptable salt thereof is administered up to three times or more a day for as long as the subject is in need of treatment for the proliferative disorder. In another aspect, the therapeutically effective amount of crenolanib or the pharmaceutically acceptable salt thereof is: provided at least one of sequentially or concomitantly, with another pharmaceutical agent to maintain remission of an existing patient; provided as a single agent or in combination with another pharmaceutical agent in a patient to maintain remission, or in a relapsed/refractory proliferative disorder patient; or provided as a single agent or in combination with another pharmaceutical agent to maintain remission, or in a relapsed/refractory proliferative disorder pediatric patient. In another aspect, the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, or crenolanib succinate.

In another embodiment, the present invention includes a method for treating a subject suffering from leukemia comprising: obtaining a sample from the subject; determining from the subject sample that the patient has a deregulated FLT3 receptor or a constitutively active FLT3 receptor; further determining that the subject is refractory to or has relapsed after administration of a prior tyrosine kinase inhibitor; administering to the subject in need of such treatment a therapeutically effective amount of crenolanib or a pharmaceutically acceptable salt thereof sufficient to treat the leukemia. In one aspect, the mutated or constitutively active FLT3 is at least one of FLT3-ITD; FLT3-TKD; an activating mutation in FLT3; a copy number gain or an amplification of the FLT3 gene; or a gene fusion comprising the fusion of FLT3 with another gene. In another aspect, the subject has been provided a prior tyrosine kinase inhibitor selected from midostaurin, sorafenib, gilteritinib, quizartinib, pexidartinib, FF-10101, CG-806, lestaurtinib, AG1295, AG1296, CEP-5214, CEP-7055, HM43239, pacritinib, MAX-40279, FYSYN, NMS-03592088, or TG02 citrate; or the subject has a FLT3 mutation that confers resistance to the prior tyrosine kinase inhibitor. In another aspect, the mutation in the FLT3 gene or change in phenotype or genotype of FLT3 is a resistance conferring mutation selected from a missense mutation occurring in at least one of amino acid residues K429, A627, N676, A680, F691, Y693, G697, D698, N701, D835, N841, Y842, A848 present alone or in combination with a FLT3-ITD mutation. In another aspect, the resistance conferring FLT3 mutation was present before administration of the prior tyrosine kinase inhibitor or wherein the resistance conferring FLT3 mutation was acquired during or after administration of the prior tyrosine kinase inhibitor. In another aspect, the leukemia is selected from at least one of: Hodgkin's disease, a myeloma, acute promyelocytic leukemia (APL), chronic lymphocytic leukemia (CLL), chronic myeloid leukemia (CML), chronic neutrophilic leukemia (CNL); acute undifferentiated leukemia (AUL), anaplastic large-cell lymphoma (ALCL), prolymphocytic leukemia (PML); juvenile myelomonocytic leukemia (JMML); adult T-cell ALL, acute myeloid leukemia (AML), AML with trilineage myelodysplasia, myelodysplastic syndromes (MDS), myeloproliferative neoplasms (MPN), or multiple myeloma (MM).

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

The present invention is directed to the administration of crenolanib, or a pharmaceutically acceptable salt thereof, to subjects suffering from a cancer in order to treat the cancer, prevent reoccurrence of the cancer, and/or prevent worsening of the cancer.

Crenolanib is an orally bioavailable TKI, targeting FLT3. It is significantly more selected for FLT3 than other kinases, including c-KIT, VEGFR2, TIE2, FGFR2, EGFR, erbB2, and SRC. (Lewis et al., 2009) As a type I TKI, it binds to both the active and inactive conformations of the kinase. Importantly, crenolanib shows preclinical activity against the quizartinib and gilteritinib resistant FLT3 mutations, including missense mutations at D835 or F691. (C. C. Smith et al., 2014) In direct enzyme inhibition assays, crenolanib was found to inhibit >99% of the kinase activity of FLT3-F691L mutants at a concentration of 10 nM. In cell lines overexpressing FLT3-F691L. crenolanib blocks phosphorylation of FLT3 at nanomolar concentrations. As such, crenolanib is ideally suited for the treatment of subjects suffering from constitutively active FLT3 proliferative disorders who have discontinued treatment with other FLT3 TKIs due to progressed disease as a result of resistance conferring secondary mutations. As a pan-FLT3 inhibitor, crenolanib has shown activity in subjects with cancers associated with FLT3 copy number gain, amplification, fusions, or constitutively active mutants.

The present invention comprises methods of inhibiting mutant or constitutively active FLT3 in a cell or a subject, or to treat disorders related to FLT3 activity or expression in a subject. In one embodiment, the present invention provides a method for reducing or inhibiting the kinase activity of mutant FLT3 in a subject comprising the step of administering a compound of the present invention to the subject. In other embodiments, the present invention provides therapeutic methods for treating a subject with a proliferative disorder driven by aberrant kinase activity of mutant FLT3. The present invention also provides methods for treating a patient suffering from a proliferative disorder that is relapsed/refractory to a prior tyrosine kinase inhibitor.

As used herein, the term "subject" refers to an animal, such as a mammal or a human, who has been the object of treatment, observation or experiment.

As used herein, the term "contacting" refers to the addition of Crenolanib or pharmaceutically acceptable salt(s) thereof, to cells such that the compound is taken up by the cell.

As used herein, the term "therapeutically effective amount" refers to an amount of Crenolanib or pharmaceutically acceptable salt(s) thereof, that elicits the biological or medicinal response in a subject that is being sought by a researcher, veterinarian, medical doctor or other clinician, which includes alleviation of the symptoms of the disease or the disorder being treated, reduction in the burden of the proliferative disorder (such as reduction in tumor size), and/or increase in progression-free or overall survival including prolonged stable disease. Methods for determining therapeutically effective doses for pharmaceutical compositions comprising a compound of the present invention are known in the art.

As used herein, the term "composition" is intended to encompass a product comprising the specified ingredients in the specified amounts, as well as any product which results, directly or indirectly, from combinations of the specified ingredients in the specified amounts.

As used herein, the term "disorder related to mutant FLT3", or "mutant FLT3 driven cell proliferative disorder" includes disease associated or implicating mutant FLT3 activity, for example, mutations leading to constitutive activation of FLT3.

As used herein, the term "cell proliferative disorders" refers to excess cell proliferation of one or more subset of cells in a multicellular organism resulting in harm (i.e., discomfort or decreased life expectancy) to the multicellular organism. Cell proliferative disorders can occur in different types of animals and humans. Examples of cell proliferative disorders are gastrointestinal stromal tumor (GIST), leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy.

As used herein, the term "relapsed/refractory" or "recurrent" refer(s) to a subject that was previously administered a pharmaceutical agent in order to treat a proliferative disease, but either did not respond to treatment (refractory), or progressed after initially responding (relapsed).

Detection of the mutation FLT3 can be performed using any suitable means known in the art. For example, detection of gene mutations can be accomplished by detecting nucleic acid molecules (such as DNA) using nucleic acid amplification methods (such as RT-PCR) or high-throughput sequencing (i.e. "next-generation sequencing"). By example, next-generation sequencing platforms such as Illumina may be used to determine the exact genetic sequence of specific genes, or portions of genes, of interest. In brief, DNA from a tumor sample is fragmented, ligated with the appropriate primers and adaptors, and amplified using PCR during "library preparation". The prepared libraries are then sequenced using one of a number of commercially available systems which generates the sequence of the chosen target genes, all exomes, or the entire genome. The sequences are then analyzed using commercial available software, which aligns the tumor sample sequence to the known sequence of the genes of interest and performs a variant calling step, which identifies differences at the DNA level in the tumor sample and determines if such mutations would result in alteration of the amino acid sequence in the translated protein. Using these systems, a person of skill in the art can determine if a subject has one of the identified mutations with in FLT3. Further information on FLT3, including full gene and protein sequences, known clinically relevant variants and mutations, tissue expression, and signaling interaction partners can be found at UniProt (accession number P36888-1), GenBank (accession number NM 04119.2), and GenPept (accession number NP_004110.2).

As used herein, the term "missense mutation" refers to alterations in the genetic sequence of the FLT3 gene that results in the substitution of one amino acid for a different amino acid when the sequence is translated into a protein.

As used herein, the term "missense mutation" refers to alterations in the genetic sequence of the FLT3 gene that results in the substitution of one amino acid for a different amino acid when the sequence is translated into a protein.

As used herein, the term "ITD" or "internal tandem duplication" refers to the insertion of nucleotides at the DNA level in which the number of nucleotides is a multiple of three, which results in the addition of amino acids at the protein level but does not shift the reading frame of the gene.

As used herein, the terms "resistance mutations", or "mutations conferring resistance", or "secondary mutations" refer to mutations other than ITD within the FLT3 gene that are not sensitive to gilteritinib, midostaurin, quizartinib or other TKIs, other than the present invention. In other words, these mutations, whether present alone or in combination with ITD, retain kinase activity when treated with midostaurin, gilteritinib, or other TKIs but are inhibited by the present invention. Non-limiting examples of resistance mutations are missense mutations at amino acid residues K429, A627, N676, A680, F691, Y693, G697, D698, N701, D835, N841, Y842, or A848. Additional mutations within the immunoglobulin-like domain, juxtamembrane domain, tyrosine kinase domains, and hinge region, are also included within the scope of the present invention.

As used herein, the term "copy number gain" or "copy number variation" refers to the presence of more than 2 but fewer than 5 copies of the FLT3 gene. As used herein "amplification" refers to a gain of more than 5 FLT3 gene copies, or signals, per cell. The number gain and/or amplification can be detected through any means known in the art. For example, fluorescence in situ hybridization (FISH), in which fluorescently labeled probes which bind to specific region of DNA are incubated with cells and the number of "signals" (the number of regions of DNA bound by the probe) are counted.

FLT3 kinase inhibitors known in the art include lestaurtinib (also known as CEP-701, Kyowa Hakko, licensed to Cephalon); CHIR-258 (Chiron Corp.); EB10 and IMC-EB10 (ImcLone Systems Inc.); Midostaurin (also known as PKC412, Novartis AG); Tandutinib (also known as MLN-518, COR Therapeutics Inc., licensed to Millennium Pharmaceuticals Inc.); Sunitinib (also known as SU11248, Pfizer USA); Quizartinib (also known as AC220, Daiichi Sankyo); XL-999 (Exelixis USA); GTP 14564 (Merck Biosciences UK); AG1295 and AG1296; CEP-5214 and CEP-7055 (Cephalon); Gilteritinib (also known as ASP2215, Astellas Pharma Inc.); FF-10101-01 (Fujifilm Pharmaceuticals); HM43239 (Hanni Pharmaceuticals); Pacritinib (also known as SB1518, CTI Biopharma); MAX-40279 (Maxinovel Pty. Ltd.); FLYSYN (Synimmune GmBH); WS-03592088 (also known as NMS-P088, Nerviano Medical Sciences); LT-171-861; and TG02 citrate (Tragara Pharmaceuticals). See also (Griswold et al., 2004; Levis et al., 2002; Levis & Small, 2004; Majothi et al., 2020; Murata et al., 2003; O'Farrell et al., 2003; B. D. Smith et al., 2004; Stone et al., 2005; Yee et al., 2002).

The aforementioned inhibitors have either been or are currently being investigated in the preclinical setting, or phase I and II trials as monotherapy in relapsed AML, or in phase III combination studies in relapsed AML. Despite reports of successful inhibition of FLT3 with these compounds in preclinical studies, complete remissions have rarely been achieved in FLT3 mutant AML patients in the clinical setting. For the majority of patients, the clinical response is short-lived. Response criteria for AML clinical trials are adapted from the International Working Group for AML (Cheson et al., 2003). Responders are patients who obtain a Complete Response (CR), Complete Response with incomplete blood count recovery (CRi), or Partial Remission (PR). Briefly, criteria are as follows:

1. Complete Remission (CR):
   a. Peripheral blood counts:
      i. No circulating blasts
      ii. Neutrophil count $\geq 1.0 \times 10^9/L$
      iii. Platelet count $\geq 100 \times 10^9/L$
   b. Bone marrow aspirate and biopsy:
      i. $\leq 5\%$ blasts
      ii. No Auer Rods
      iii. No extramedullary leukemia
2. Complete remission with incomplete blood count recovery (CRi):
   a. Peripheral blood counts:
      i. No circulating blasts
      ii. Neutrophil count $<1.0 \times 10^9/L$, or
      iii. Platelet count $<100 \times 10^9/L$
   b. Bone marrow aspirate and biopsy
      i. $\leq 5\%$ blasts
      ii. No Auer Rods
      iii. No extramedullary leukemia
3. Partial remission:
   a. All CR criteria if abnormal before treatment except:
   b. $\geq 50\%$ reduction in bone marrow blast but still >5%

To date, clinical responses to FLT3 inhibitors have been primarily limited to clearance of peripheral blood (PB) blasts, which frequently return within a matter of weeks, while bone marrow (BM) blasts remain largely unaffected. For example, treatment with sorafenib, the prior mentioned multi-kinase inhibitor with activity against mutant FLT3, while effective in clearing PB blasts, has resulted in only modest BM blast reductions (Borthakur et al., 2011). BM blast percentage plays a central role in the diagnosis and classification of AML. The presence of a heightened percentage of blasts in BM is associated with significantly shorter overall survival (Amin et al., 2005; Small, 2006). To effectively treat FLT3 mutated AML patients and overcome the significant unmet need in this patient population, an inhibitor is required that significantly depletes both PB and BM blasts, bridges high risk and heavily pretreated patients to stem cell transplant, and can help to decrease relapse rates and increase overall survival in early stage disease patients.

As used herein, the term "proliferative disorder burden" or "proliferative disease burden" refers to the overall impact on the health of a subject or patient that has cancer. The impact on the health of the subject or patient, when compared to a subject that does not have the proliferative disorder or disease, can include, e.g., a reduction in the overall span of life, an increase in years with a disability of disease, a reduction in wellness or overall health, to name a few.

In one embodiment, the present invention therapeutically effective amounts of the compound having Formula I:

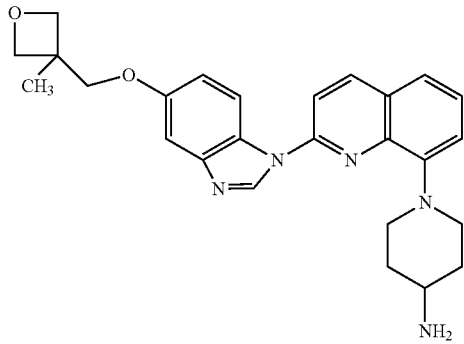 [SMILES: CC1(COc2ccc3c(c2)ncn3-c2ccc3cccc(N4CCC(N)CC4)c3n2)COC1]

or a pharmaceutically acceptable salt or solvate thereof, in a therapeutically effective amount against a proliferative disease is selected from at least one of gastrointestinal stromal tumor, leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. Pharmaceutically acceptable salts such as hydrochloride, phosphate and lactate are prepared in a manner similar to the benzenesulfonate salt and are well known to those of moderate skill in the art. Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and are in no way meant to limit the invention, including Crenolanib as Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate.

Compounds of the present invention may be administered to a subject systemically, for example, orally, intravenously, subcutaneously, intramuscular, intradermal or parenterally. The compounds of the present invention can also be administered to a subject locally.

Compounds of the present invention may be formulated for slow-release or fast-release with the objective of maintaining contact of compounds of the present invention with targeted tissues for a desired range of time.

Compositions suitable for oral administration include solid forms, such as pills, tablets, caplets, capsules, granules, and powders, liquid forms, such as solutions, emulsions, and suspensions. Forms useful for parenteral administration include sterile solutions, emulsions and suspensions.

The daily dosage of the compounds of the present invention may be varied over a wide range from 50 to 500 mg per adult human per day. For oral administration, the compositions are preferably provided in the form of tablets containing 20 and 100 milligrams. The compounds of the present invention may be administered on a regimen up to three times or more per day. Preferably three times per day. Optimal doses to be administered may be determined by those skilled in the art, and will vary with the compound of the present invention used, the mode of administration, the time of administration, the strength of the preparation, the details of the disease condition. Factors associated with patient characteristics, such as age, weight, and diet will call for dosage adjustments. In other examples, the daily dosage of the compounds of the present invention may be varied over a wide range from 15 to 500, 25 to 450, 50 to 400, 100 to 350, 150 to 300, 200 to 250, 15, 25, 50, 75, 100, 150, 200, 250, 300, 400, 450, or 500 mg per day. The compounds of the present invention may be administered on a daily regimen, once, twice, three or more times per day. Optimal doses to be administered may be determined by those skilled in the art, and will vary with the compound of the present invention used, the mode of administration, the time of administration, the strength of the preparation, the details of the disease condition. One or more factors associated with subject characteristics, such as age, weight, and diet will call for dosage adjustments. Techniques and compositions for making useful dosage forms using the Crenolanib are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); relevant portions incorporated herein by reference.

A dosage unit for use of Crenolanib, may be a single compound or mixtures thereof with other compounds, e.g., a potentiator. The compounds may be mixed together, form ionic or even covalent bonds. The compounds of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the Crenolanib of the present invention to a patient in need of therapy.

The Crenolanib is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices Depending on the best location for administration, the Crenolanib may be formulated to provide, e.g., maximum and/or consistent dosing for the particular form for oral, rectal, topical, intravenous injection or parenteral administration. While the Crenolanib may be administered alone, it will generally be provided in a stable salt form mixed with a pharmaceutically acceptable carrier. The carrier may be solid or liquid, depending on the type and/or location of administration selected.

Preparation of the compounds of the present invention. General synthetic methods, which may be referred to for preparing the compounds of Formula I are provided in U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application No. US 2005/0124599 (Pfizer, Inc.) and U.S. Pat. No. 7,183,414 (Pfizer, Inc.), relevant portions incorporated herein by reference.

Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and are in no way meant to limit the invention.

Summary of Examples

Example A: Patient harbored FLT3-ITD and FLT3 F691 mutations. Following progression on two prior FLT3 tyrosine kinase inhibitors, midostaurin and gilteritinib, and cytotoxic chemotherapy, the patient achieved complete clearance of leukemic blasts in the blood, bone marrow, and central nervous system (CNS) after crenolanib besylate combination therapy.

Example B: Patient harbored a FLT3-ITD mutation that persisted following progression on a prior FLT3 tyrosine kinase inhibitor, gilteritinib, and cytotoxic chemotherapy. The patient achieved complete remission with full count recovery after crenolanib besylate combination therapy.

Example C: Patient harbored a FLT3-ITD mutation that persisted following progression on two prior FLT3 tyrosine kinase inhibitors, midostaurin and gilteritinib, and cytotoxic chemotherapy. The patient achieved complete remission and was bridged to hematopoietic stem cell transplant after crenolanib besylate combination therapy.

Example D: Patient harbored a FLT3-ITD mutation. Following progression on three prior FLT3 tyrosine kinase inhibitors, sorafenib, gilteritinib and midostaurin, and cytotoxic chemotherapy, the patient achieved complete remission with incomplete count recovery after crenolanib besylate combination therapy.

Example E: Patient harbored FLT3-ITD, FLT3 D835, and FLT3 Y842 mutations. Following progression on a prior FLT3 tyrosine kinase inhibitor, sorafenib, and cytotoxic chemotherapy, the patient achieved partial remission after crenolanib besylate monotherapy.

Example F: Patient harbored FLT3-ITD, FLT3 D835, and FLT3 N841 mutations. Following progression on a prior FLT3 tyrosine kinase inhibitor, sorafenib, and cytotoxic chemotherapy, the patient achieved complete remission with incomplete hematologic recovery after crenolanib besylate monotherapy.

Example A: The effect of crenolanib besylate therapy in a relapsed/refractory patient with an acquired resistance conferring FLT3 mutation after prior midostaurin and gilteritinib administration: achievement of clearance of blood, bone marrow, and CNS leukemic blasts.

A 54-year-old female was diagnosed with relapsed AML positive for FLT3-ITD and a FLT3-F691 missense mutation, specifically F691L. This mutation, sometimes referred to as a "gatekeeper" mutation, is known to confer resistance to the FLT3 tyrosine kinase inhibitor gilteritinib, among others. (McMahon et al., 2019)

The patient was initially diagnosed with FLT3-ITD positive AML in March of 2019 and was treated with a standard chemotherapy regimen plus the FLT3 inhibitor midostaurin, achieving a complete remission after two cycles. The patient relapsed approximately 6 months later, in October 2019, at which point the patient remained FLT3 positive and received a salvage combination therapy regimen which included the FLT3 inhibitor gilteritinib. The patient achieved a partial remission to this regimen and remained stable but experienced disease progression in May 2020, at which point they were enrolled on a phase I clinical trial of a menin inhibitor. After 1 month on study, the patient experienced significant disease progression, including CNS involvement, and was removed from study.

At this point, June 2020, the patient had received 3 prior lines of therapy, including two FLT3 inhibitors. Molecular testing revealed that the patient had acquired a secondary resistance conferring FLT3 mutation, F691L, after gilteritinib treatment. The persistence of the FLT3-ITD mutation, acquisition of the F691L mutation, and the fact that the patient was relapsed/refractory to multiple FLT3 inhibitors put this patient in a particularly high-risk group, associated with a decreased likelihood of response to treatment and shortened overall survival. (Perl et al., 2021)

With no other approved standard treatment options available, the treating physicians submitted a request for compassionate use of crenolanib besylate, which was granted in June 2020. The patient was treated with salvage chemotherapy comprised of high dose cytarabine and crenolanib besylate at 80 mg three times daily. At the start of treatment, the patient had 72% bone marrow blasts, 23% peripheral blasts, and 88% blasts (of all nucleated cells) in the cerebral spinal fluid (CSF), indicating significant CNS involvement of their leukemia.

Bone marrow, peripheral blood, and CSF samples taken on day 21 of treatment revealed complete clearance of leukemic blasts from all three compartments. Molecular testing revealed clearance of all FLT3 clones in the bone marrow. A second bone marrow biopsy taken on day 43 of treatment confirmed that the patient remained in a morphological leukemia free state (a complete remission without count recovery) and free from CNS leukemia. The patient remained on treatment for over 90 days, and died in remission 3.5 months after starting crenolanib therapy due to sepsis.

Table A below illustrates the ability of crenolanib to clear malignant leukemia blasts from the bone marrow, peripheral blood, and CSF of a patient with a resistance conferring FLT3 mutation after prior tyrosine kinase inhibitor treatment.

| Days on Crenolanib | Bone Marrow Blast %) | Peripheral Blast (%) | CSF Blast (%) |
|---|---|---|---|
| 0 | 72% | 23% | 88% |
| 21 | <5% | 0% | 0% |
| 43 | <5% | Not Done | 0% |

Example B: The effect of crenolanib besylate therapy in a relapsed/refractory patient who was refractory to gilteritinib treatment: achievement of complete remission with full count recovery.

A 35-year-old female was diagnosed with relapsed AML positive for a FLT3-ITD mutation. The patient was initially diagnosed with FLT3-ITD positive AML in March 2018, and was treated with a standard chemotherapy regimen, achieving a complete remission.

The patient relapsed approximately 3 months later, in June 2018, and received the FLT3 inhibitor gilteritinib as salvage therapy. The patient was refractory to this treatment, with persistent 20% bone marrow blasts after 2 cycles of gilteritinib therapy. The patient also experienced pericarditis as a side effect to gilteritinib treatment. After discontinuation of gilteritinib, the patient received standard salvage chemotherapy, achieved a second remission, and received a hematopoietic stem cell transplant in November 2018. Approximately 17 months later the patient relapsed with FLT3-ITD positive disease.

At this point, April 2020, the patient had received 3 prior lines of therapy, including the FLT3 inhibitor gilteritinib. Molecular testing revealed that the patient's initial FLT3-ITD mutation persisted. The persistence of this mutation and the fact that the patient had relapsed after HSCT put this patient in a particularly high-risk group, associated with a decreased likelihood of response to treatment and shortened overall survival. (Bejanyan et al., 2015).

With few treatment options available, the treating physicians submitted a request for compassionate use of crenolanib besylate, which was granted in April 2020. The patient was treated with salvage chemotherapy comprised of fludarabine, cytarabine, idarubicin, and granulocyte colony stimulating factor followed by crenolanib besylate at 100 mg three times daily. At the start of treatment, the patient had 75% bone marrow blasts, 85% peripheral blasts, and diagnostic imaging showed extramedullary disease (leukemic blasts outside the bone marrow or blood) in the spleen and lymph nodes.

A bone marrow biopsy obtained on day 36 of treatment revealed complete clearance of peripheral blasts, clearance of bone marrow blasts to less than 5%, and recovery of neutrophils and platelets, categorized as a complete remission with full count recovery. Molecular testing revealed clearance of all FLT3 clones. A second bone marrow biopsy obtained on day 81 of treatment confirmed the patient remained in complete remission and had a complete clearance of all extramedullary disease. The patient remained in remission for over 4 months on crenolanib besylate therapy.

Table B below illustrates the ability of crenolanib to clear malignant leukemia blasts from the bone marrow and peripheral blood of a patient with relapsed/refractory disease after prior tyrosine kinase inhibitor treatment.

| Days on Crenolanib | Bone Marrow Blast (%) | Peripheral Blast (%) |
|---|---|---|
| 0 | 75% | 85% |
| 36 | <5% | 0% |
| 81 | <5% | 0% |

Example C: The effect of crenolanib besylate therapy in a relapsed/refractory patient with a FLT3-ITD mutation after prior gilteritinib administration: achievement of complete remission with full count recovery and bridge to transplant.

A 22-year-old female was diagnosed with relapsed AML positive for a FLT3-ITD mutation. The patient was initially diagnosed with FLT3-ITD mutated AML in November 2019, and was treated with a standard chemotherapy regimen comprising cytarabine and daunorubicin plus the FLT3 inhibitor midostaurin, achieving a complete remission after two cycles, though the patient remained MRD (measurable residual disease) and FLT3 positive. The patient then received high dose cytarabine consolidation therapy, in combination with midostaurin but the MRD and FLT3-ITD mutation persisted. In May 2020, as the FLT3-ITD mutation was still detectable in bone marrow samples obtained from the patient, the patient was administered the FLT3 inhibitor gilteritinib in an effort to eliminate the remaining FLT3-ITD positive blasts, as they could potentially cause relapse. A bone marrow biopsy performed after 4 weeks of single agent gilteritinib therapy found that the patient had relapsed, with 40% bone marrow blasts, and gilteritinib was discontinued.

At this point, June 2020, the patient had received 2 prior lines of therapy including two FLT3 inhibitors. Molecular testing confirmed that the FLT3-ITD mutation present at diagnosis had persisted through all lines of therapy (more in-depth sequencing, including the testing that would reveal the presence of resistance conferring point mutations, was not performed). The persistence of the FLT3-ITD mutation and the fact that the patient was relapsed/refractory to multiple FLT3 inhibitors put this patient in a particularly high-risk group, associated with a decreased likelihood of response to treatment and shortened overall survival. (Perl et al., 2021)

With no other approved standard treatment options available, the treating physicians submitted a request for compassionate use of crenolanib besylate, which was granted in June 2020. The patient was treated with salvage chemotherapy comprised of fludarabine, cytarabine, idarubicin, and granulocyte colony stimulating factor followed by crenolanib besylate at 100 mg three times daily. At the start of treatment, the patient had 43% bone marrow blasts.

A bone marrow biopsy sample obtained on day 56 of treatment found that the bone marrow blast percentage had fallen to less than 5% and the patient received a hematopoietic stem cell transplant. The patient then received single agent crenolanib besylate therapy as post-transplant maintenance starting 49 days after transplant, in an effort to prevent another relapse. A bone marrow biopsy performed 30 days after transplant, before beginning crenolanib maintenance therapy, found that the patient remained in remission but that the FLT3-ITD mutation was still detectable. A second bone marrow biopsy performed 68 days after transplant, 19 days after beginning crenolanib maintenance, revealed that the FLT3-ITD mutation had been cleared.

Table C below illustrates the ability of crenolanib to clear malignant leukemia blasts from the bone marrow of a patient relapsed/refractory to two prior tyrosine kinase inhibitors, and the ability of crenolanib to clear FLT3-ITD MRD post-hematopoietic stem cell transplant.

| Days on Crenolanib | Bone Marrow Blast (%) | FLT3-ITD Status |
|---|---|---|
| 6 | 43% | Positive |
| 56 | <5% | Positive |
| Post-Transplant—Maintenance Started Day 49 | | |
| Day 30 | <5% | Positive |
| Day 68 | <5% | Negative |

Example D: The effect of crenolanib besylate therapy in a relapsed/refractory patient with a FLT3-ITD mutation after prior sorafenib, gilteritinib, and midostaurin administration: achievement of complete remission with incomplete count recovery.

A 76-year-old male was diagnosed with relapsed AML positive for a FLT3-ITD mutation. The patient was initially diagnosed with myelodysplastic syndrome in 2008, which transformed into FLT3-ITD mutated AML in August 2015. At the time of transformation into AML, the patient was treated with a standard chemotherapy regimen and achieved a complete remission and proceeded to a hematopoietic stem cell transplant. Approximately 9 months after transplant, in August 2016, the patient relapsed with CNS involvement of his leukemia and was treated with cytarabine, methotrexate, and the FLT3 inhibitor sorafenib, once again achieving remission. Two and a half years later, in April 2019, the patient relapsed, again with CNS involvement. The patient was treated with venetoclax, donor lymphocyte infusion (a common salvage method for patients relapsing after hematopoietic stem cell transplant in which white blood cells from the original transplant donor are infused into the recipient), and the FLT3 inhibitor gilteritinib, again achieving complete remission. Seven months later, in November 2019, the patient once again relapse with CNS involvement and received cytarabine, cladribine, and a third FLT3 inhibitor, midostaurin, again achieving CR. Eight months later, in July 2020, the patient relapsed for a fourth time, with 16% bone marrow blasts and the persistence of the original FLT3-ITD mutation.

At this point, July 2020, the patient had received 4 prior lines of therapy, including three FLT3 inhibitors. Molecular testing confirmed that the FLT3-ITD mutation present at diagnosis had persisted through all lines of therapy (more in-depth sequencing, including the testing that would reveal the presence of resistance conferring point mutations, was not performed). The persistence of the FLT3-ITD mutation and the fact that the patient was relapsed/refractory to multiple FLT3 inhibitors put this patient in a particularly high-risk group, associated with a decreased likelihood of response to treatment and shortened overall survival. (Perl et al., 2021)

With no other approved standard treatment options available, the treating physicians submitted a request for compassionate use of crenolanib besylate, which was granted in July 2020. The patient was treated with salvage chemotherapy comprised of fludarabine, cytarabine, idarubicin, and granulocyte colony stimulating factor followed by crenolanib besylate at 100 mg three times daily. At the start of treatment, the patient had 16% bone marrow blasts.

A bone marrow biopsy obtained on day 21 of treatment revealed the clearance of bone marrow blasts to less than 5% with neutrophil count recovery, categorized as a complete remission with incomplete hematologic recovery. At this time, the FLT3-ITD mutation was also cleared. Due to the patient's advanced age, regular bone marrow biopsies were not obtained, and the patient remained on crenolanib treatment for approximately 6 months.

Patient Example D illustrates the ability of crenolanib to clear leukemia blasts from the bone marrow of a patient relapsed/refractory to three prior FLT3 tyrosine kinase inhibitors.

Example E: The effect of crenolanib besylate monotherapy in a relapsed/refractory patient with acquired resistance conferring FLT3 mutations after prior sorafenib administration: achievement of partial remission.

An 87-year-old female was diagnosed with relapsed AML positive for FLT3-ITD, and FLT3-D835 and Y842 missense mutation, specifically D835Y and Y842C. These mutations are known to confer resistance to the FLT3 tyrosine kinase inhibitors sorafenib and quizartinib, among others. (Wang et al., 2021).

The patient was initially diagnosed with FLT3-ITD AML in August 2013 and was treated with a standard chemotherapy regimen, achieving a complete remission after two cycles. In an attempt to prevent relapse, the patient was given sorafenib as maintenance therapy. The patient relapsed 5 months later, in March 2014.

At this point, molecular testing revealed the persistence of the original FLT3-ITD mutation, as well as the acquisition of the secondary resistance conferring FLT3 mutations D835Y and Y842C after sorafenib treatment. The persistence of the FLT3-ITD mutation, acquisition of the D835Y and Y842C mutations, and the fact that the patient had relapsed to a prior FLT3 inhibitor put this patient in a particularly high-risk group, associated with a decreased likelihood of response to treatment and shortened overall survival. (Perl et al., 2021)

With no other approved standard treatment options available, the patient was enrolled on a clinical trial of crenolanib besylate monotherapy administered at 100 mg three times daily (NCT01657682). At study enrollment, the patient had 68% bone marrow blasts and 30% peripheral blasts.

A bone marrow biopsy obtained on day 27 of treatment revealed that the patient's bone marrow blasts had decreased to 7% and that peripheral blasts had been cleared, categorized as a partial remission. Unfortunately, the patient passed away due leukemia related complications on day 61 of treatment before further bone marrow biopsies were obtained.

Patient example E illustrates the ability of crenolanib to significantly reduce malignant leukemia blasts in the bone marrow, from 30% to 7%, and completely clear malignant leukemia blasts in the peripheral blood of a patient with two resistance conferring FLT3 mutations after prior tyrosine kinase inhibitor treatment.

Example F: The effect of crenolanib besylate monotherapy in a relapsed/refractory patient with acquired resistance conferring FLT3 mutations after prior sorafenib administration: achievement of complete remission with incomplete hematologic recovery.

A 31-year-old male was diagnosed with relapsed/refractory AML positive for FLT3-ITD, and FLT3-D835 and N841 missense mutations, specifically D835V, D835Y, D835H, and N841K. These mutations are known to confer resistance to the FLT3 tyrosine kinase inhibitors sorafenib and quizartinib, among others. (Wang et al., 2021).

The patient was initially diagnosed with FLT3-ITD AML in November 2012 and was treated with a standard chemotherapy regimen, achieving a complete remission and proceeding to hematopoietic stem cell transplant. Six months after transplant, in November 2013, the patient relapsed and was treated with sorafenib and decitabine as salvage therapy but did not respond to treatment after multiple cycles.

At this point, in May 2014, molecular testing revealed the persistence of the original FLT3-ITD mutation, as well as the acquisition of multiple secondary resistance conferring FLT3 mutations after sorafenib treatment: D835V, D835Y, D835H, and N841K. The persistence of the FLT3-ITD mutation, acquisition of the D835 and N841 mutations, and the fact that the patient had relapsed to a prior FLT3 inhibitor put this patient in a particularly high-risk group, associated with a decreased likelihood of response to treatment and shortened overall survival. (Perl et al., 2021).

With no other approved standard treatment options available, the patient was enrolled on a clinical trial of crenolanib besylate monotherapy administered at 100 mg three times daily (NCT01657682). At study enrollment, the patient had 84% bone marrow blasts and 96% peripheral blasts.

A bone marrow biopsy obtained on day 29 of treatment revealed that the patient's bone marrow blasts had fallen to 23%, with clearance of peripheral blasts, categorized as a partial remission. A second bone marrow biopsy obtained on day 57 of treatment revealed the patient's bone marrow blasts had fallen to 7%, still categorized as a partial remission. A third bone marrow biopsy obtained on day 84 of treatment revealed the patient's bone marrow blasts had fallen to less than 5%, with recovery of neutrophils, categorized a complete remission with incomplete hematologic recovery.

Table F below illustrates the ability of crenolanib to clear malignant leukemia blasts from the bone marrow of a patient with resistance conferring FLT3 mutations after prior tyrosine kinase inhibitor treatment.

| Days on Crenolanib | Bone Marrow Blast (%) |
| --- | --- |
| 0 | 84% |
| 29 | 23% |
| 57 | 7% |
| 84 | <5% |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±0.1, 0.5, 1, 2, 3, 4, 5, 6, 7, 10, 12 or 15%, or as understood to be within a normal tolerance in the art, for example, within 2 standard deviations of the mean. Unless otherwise clear from the context, all numerical values provided herein are modified by the term about.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Altman, J. K., Perl, A. E., Hill, J. E., Rosales, M., Bahceci, E., & Levis, M. J. (2021). The impact of FLT3 mutation clearance and treatment response after gilteritinib therapy on overall survival in patients with FLT3 mutation-positive relapsed/refractory acute myeloid leukemia. Cancer Med, 10(3), 797-805. doi:10.1002/cam4.3652

Amin, H. M., Yang, Y., Shen, Y., Estey, E. H., Giles, F. J., Pierce, S. A., . . . Albitar, M. (2005). Having a higher blast percentage in circulation than bone marrow: clinical implications in myelodysplastic syndrome and acute lymphoid and myeloid leukemias. Leukemia, 19(9), 1567-1572. doi:10.1038/sj.leu.2403876

Bejanyan, N., Weisdorf, D. J., Logan, B. R., Wang, H. L., Devine, S. M., de Lima, M., . . . Zhang, M. J. (2015). Survival of patients with acute myeloid leukemia relapsing after allogeneic hematopoietic cell transplantation: a center for international blood and marrow transplant research study. Biol Blood Marrow Transplant, 21(3), 454-459. doi:10.1016/j.bbmt.2014.11.007

Borthakur, G., Kantarjian, H., Ravandi, F., Zhang, W., Konopleva, M., Wright, J. J., . . . Cortes, J. E. (2011). Phase I study of sorafenib in patients with refractory or relapsed acute leukemias. Haematologica, 96(1), 62-68. doi:10.3324/haematol.2010.030452.

Cheson, B. D., Bennett, J. M., Kopecky, K. J., Buchner, T., Willman, C. L., Estey, E. H., . . . Reporting Standards for Therapeutic Trials in Acute Myeloid, L. (2003). Revised recommendations of the International Working Group for Diagnosis, Standardization of Response Criteria, Treatment Outcomes, and Reporting Standards for Therapeutic Trials in Acute Myeloid Leukemia. J Clin Oncol, 21(24), 4642-4649. doi: 10.1200/JCO.2003.04.036.

DiNardo, C., & Lachowiez, C. (2019). Acute Myeloid Leukemia: from Mutation Profiling to Treatment Decisions. Curr Hematol Malig Rep. doi:10.1007/s11899-019-00535-7.

Dohner, H., Estey, E., Grimwade, D., Amadori, S., Appelbaum, F. R., Buchner, T., . . . Bloomfield, C. D. (2017). Diagnosis and management of AML in adults: 2017 ELN recommendations from an international expert panel. Blood, 129(4), 424-447. doi:10.1182/blood-2016-08-733196.

FDA. (2019). Gilteritinib FDA SUPPL-1. Retrieved from https://www.accessdata.fda.gov/drugsatfda_docs/label/2019/211349s001lbl. pdf.

FDA. (2020). Rydapt FDA Label Suppl-4 (March 2020). Retrieved from https://www.accessdata.fda.gov/drugsatfda_docs/label/2020/207997s004lbl.pdf.

Gilliland, D. G., & Griffin, J. D. (2002). The roles of FLT3 in hematopoiesis and leukemia. Blood, 100(5), 1532-1542. doi:10.1182/blood-2002-02-0492.

Griswold, I. J., Shen, L. J., La Rosee, P., Demehri, S., Heinrich, M. C., Braziel, R. M., . . . Deininger, M. W. (2004). Effects of MLN518, a dual FLT3 and KIT inhibitor, on normal and malignant hematopoiesis. Blood, 104(9), 2912-2918. doi:10.1182/blood-2003-05-1669

Joshi, S. K., Sharzehi, S., Pittsenbarger, J., Bottomly, D., Tognon, C. E., McWeeney, S. K., . . . Traer, E. (2021). A noncanonical FLT3 gatekeeper mutation disrupts gilteritinib binding and confers resistance. Am J Hematol, 96(7), E226-E229. doi:10.1002/ajh.26174.

Levis, M., Allebach, J., Tse, K. F., Zheng, R., Baldwin, B. R., Smith, B. D., . . . Small, D. (2002). A FLT3-targeted tyrosine kinase inhibitor is cytotoxic to leukemia cells in vitro and in vivo. Blood, 99(11), 3885-3891. Retrieved from https://www.ncbi.nlm.nih.gov/pubmed/12010785.

Levis, M., & Small, D. (2004). Small molecule FLT3 tyrosine kinase inhibitors. Curr Pharm Des, 10(11), 1183-1193. doi:10.2174/1381612043452604.

Lewis, N. L., Lewis, L. D., Eder, J. P., Reddy, N. J., Guo, F., Pierce, K. J., . . . Cohen, R. B. (2009). Phase I study of the safety, tolerability, and pharmacokinetics of oral CP-868,596, a highly specific platelet-derived growth factor receptor tyrosine kinase inhibitor in patients with advanced cancers. J Clin Oncol, 27(31), 5262-5269. doi:10.1200/JCO.2009.21.8487.

Majothi, S., Adams, D., Loke, J., Stevens, S. P., Wheatley, K., & Wilson, J. S. (2020). FLT3 inhibitors in acute myeloid leukaemia: assessment of clinical effectiveness, adverse events and future research—a systematic review and meta-analysis. Syst Rev, 9(1), 285. doi:10.1186/s13643-020-01540-1.

McMahon, C. M., Ferng, T., Canaani, J., Wang, E. S., Morrissette, J. J., Eastburn, D. J., . . . Perl, A. E. (2019). Clonal selection with Ras pathway activation mediates secondary clinical resistance to selective FLT3 inhibition in acute myeloid leukemia. Cancer Discov. doi:10.1158/2159-8290.CD-18-1453.

Murata, K., Kumagai, H., Kawashima, T., Tamitsu, K., Irie, M., Nakajima, H., . . . Kitamura, T. (2003). Selective cytotoxic mechanism of GTP-14564, a novel tyrosine kinase inhibitor in leukemia cells expressing a constitutively active Fms-like tyrosine kinase 3 (FLT3). J Biol Chem, 278(35), 32892-32898. doi:10.1074/jbc.M210405200.

O'Farrell, A. M., Abrams, T. J., Yuen, H. A., Ngai, T. J., Louie, S. G., Yee, K. W., . . . Cherrington, J. M. (2003). SU11248 is a novel FLT3 tyrosine kinase inhibitor with potent activity in vitro and in vivo. Blood, 101(9), 3597-3605. doi:10.1182/blood-2002-07-2307.

Papaemmanuil, E., Gerstung, M., Bullinger, L., Gaidzik, V. I., Paschka, P., Roberts, N. D., . . . Campbell, P. J. (2016). Genomic Classification and Prognosis in Acute Myeloid Leukemia. N Engl J Med, 374(23), 2209-2221. doi:10.1056/NEJMoa1516192.

Perl, A. E., Altman, J. K., Hosono, N., Montesinos, P., Podoltsev, N., Martinelli, G., . . . Tiu, R. V. (2021). AML-091: Clinical Outcomes in Patients with Relapsed/Refractory Acute Myeloid Leukemia Treated with Gilteritinib Who Received Prior Midostaurin or Sorafenib. Clinical Lymphoma Myeloma and Leukemia, 21, 5280. doi:https://doi.org/10.1016/S2152-2650(21)01674-8.

Perl, A. E., Martinelli, G., Cortes, J. E., Neubauer, A., Berman, E., Paolini, S., . . . Levis, M. J. (2019). Gilteritinib or Chemotherapy for Relapsed or Refractory FLT3-Mutated AML. New England Journal of Medicine, 381(18), 1728-1740. doi:10.1056/NEJMoa1902688.

Rucker, F. G., Du, L., Luck, T. J., Benner, A., Krzykalla, J., Gathmann, I., . . . Dohner, K. (2021). Molecular landscape and prognostic impact of FLT3-ITD insertion site in acute myeloid leukemia: RATIFY study results. Leukemia. doi:10.1038/s41375-021-01323-0.

Sakaguchi, M., Yamaguchi, H., Kuboyama, M., Najima, Y., Usuki, K., Ueki, T., . . . Inokuchi, K. (2019). Significance of FLT3-tyrosine kinase domain mutation as a prognostic factor for acute myeloid leukemia. Int J Hematol. doi:10.1007/s12185-019-02720-z.

Schmalbrock, L. K., Dolnik, A., Cocciardi, S., Strang, E., Theis, F., Jahn, N., . . . Bullinger, L. (2021). Clonal evolution of acute myeloid leukemia with FLT3-ITD mutation under treatment with midostaurin. Blood. doi:10.1182/blood.2020007626.

Small, D. (2006). FLT3 mutations: biology and treatment. Hematology Am Soc Hematol Educ Program, 178-184. doi:10.1182/asheducation-2006.1.178.

Smith, B. D., Levis, M., Beran, M., Giles, F., Kantarjian, H., Berg, K., . . . Small, D. (2004). Single-agent CEP-701, a novel FLT3 inhibitor, shows biologic and clinical activity in patients with relapsed or refractory acute myeloid leukemia. Blood, 103(10), 3669-3676. doi:10.1182/blood-2003-11-3775.

Smith, C. C., Lasater, E. A., Lin, K. C., Wang, Q., McCreery, M. Q., Stewart, W. K., . . . Shah, N. P. (2014). Crenolanib is a selective type I pan-FLT3 inhibitor. Proc Natl Acad Sci USA, 111(14), 5319-5324. doi:10.1073/pnas.1320661111.

Smith, C. C., Lin, K., Stecula, A., Sali, A., & Shah, N. P. (2015). FLT3 D835 mutations confer differential resistance to type II FLT3 inhibitors. Leukemia, 29(12), 2390-2392. doi:10.1038/leu.2015.165.

Stirewalt, D. L., & Radich, J. P. (2003). The role of FLT3 in haematopoietic malignancies. Nat Rev Cancer, 3(9), 650-665. doi:10.1038/nrc1169.

Stone, R. M., DeAngelo, D. J., Klimek, V., Galinsky, I., Estey, E., Nimer, S. D., . . . Griffin, J. D. (2005). Patients with acute myeloid leukemia and an activating mutation in FLT3 respond to a small-molecule FLT3 tyrosine kinase inhibitor, PKC412. Blood, 105(1), 54-60. doi:10.1182/blood-2004-03-0891.

Tyner, J. W., Tognon, C. E., Bottomly, D., Wilmot, B., Kurtz, S. E., Savage, S. L., . . . Druker, B. J. (2018). Functional genomic landscape of acute myeloid leukaemia. Nature. doi:10.1038/s41586-018-0623-z.

Wang, Z., Cai, J., Cheng, J., Yang, W., Zhu, Y., Li, H., . . . Lu, S. (2021). FLT3 Inhibitors in Acute Myeloid Leukemia: Challenges and Recent Developments in Overcoming Resistance. J Med Chem, 64(6), 2878-2900. doi:10.1021/acs.jmedchem.0c01851.

Yee, K. W., O'Farrell, A. M., Smolich, B. D., Cherrington, J. M., McMahon, G., Wait, C. L., . . . Heinrich, M. C. (2002). SU5416 and SU5614 inhibit kinase activity of wild-type and mutant FLT3 receptor tyrosine kinase. Blood, 100(8), 2941-2949. doi:10.1182/blood-2002-02-0531.

What is claimed is:

1. A method for treating a subject suffering from a hematological malignancy, the method comprising the steps of:
   determining whether the subject has increased FLT3 tyrosine kinase activity by:
   obtaining or having obtained a biological sample from the patient; and
   performing or having performed an assay on the biological sample to determine if the patient has a gene mutation in the FLT3 gene, a change in the kinase activity of the FLT3 tyrosine kinase, overexpression of the FLT3 tyrosine kinase, or a change in a phenotype or genotype of the FLT3 tyrosine kinase, wherein the mutation in the FLT3 gene or change in phenotype or genotype of FLT3 is a resistance-conferring mutation selected from a missense mutation occurring in at least one of amino acid residues K429, A627, N676, A680, F691, Y693, G697, D698, N701, D835, N841, Y842, A848 present alone or in combination with a FLT3-ITD mutation;

treating the subject with a first tyrosine kinase inhibitor; and if the patient is refractory to or relapses after treatment with the first tyrosine kinase inhibitor, and the patient has a gene mutation in FLT3; a change in the kinase activity of FLT3, overexpression of FLT3, or a change in the phenotype or genotype of FLT3 tyrosine kinase, then discontinuing administration of the first tyrosine kinase inhibitor and internally administering crenolanib to the patient in an effective amount to reduce a hematological malignancy burden or to prevent proliferative disease the hematological malignancy progression.

2. The method of claim 1, wherein at least one of:
the mutated or constitutively active FLT3 is at least one of FLT3-ITD; FLT3-TKD; an activating mutation in FLT3; a copy number gain or an amplification of the FLT3 gene; or a gene fusion comprising the fusion of FLT3 with another gene;
or
a resistance-conferring FLT3 mutation was present before administration of the prior tyrosine kinase inhibitor or wherein the resistance conferring FLT3 mutation was acquired during or after administration of the prior tyrosine kinase inhibitor.

3. The method of claim 1, wherein the subject has been provided a prior tyrosine kinase inhibitor selected from midostaurin, sorafenib, gilteritinib, quizartinib, pexidartinib FF-10101, CG-806, lestaurtinib, AG1295, AG1296, CEP-5214, CEP-7055, HM43239, pacritinib, MAX-40279, FYSYN, NMS-03592088, or TG02 citrate; or the subject has a FLT3 mutation that confers resistance to the prior tyrosine kinase inhibitor.

4. The method of claim 1, wherein the hematological malignancy is selected from at least one of a leukemia, myeloma, myeloproliferative disease, and myelodysplastic syndrome.

5. The method of claim 1, wherein at least one of:
a therapeutically effective amount of crenolanib or a pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day;
a therapeutically effective amount of crenolanib or a pharmaceutically acceptable salt thereof is administered at least one of continuously, intermittently, systemically, or locally;
a therapeutically effective amount of crenolanib or a pharmaceutically acceptable salt thereof is administered orally, intravenously, or intraperitoneally;
a therapeutically effective amount of crenolanib or a pharmaceutically acceptable salt thereof is administered up to three times or more a day for as long as the subject is in need of treatment for the proliferative disorder;
a therapeutically effective amount of crenolanib or a pharmaceutically acceptable salt thereof is:
provided at least one of sequentially or concomitantly, with another pharmaceutical agent to maintain remission of an existing patient;
provided as a single agent or in combination with another pharmaceutical agent in a patient to maintain remission, or in a relapsed/refractory proliferative disorder patient; or
provided as a single agent or in combination with another pharmaceutical agent to maintain remission, or in a relapsed/refractory proliferative disorder pediatric patient; or
the crenolanib or a pharmaceutically acceptable salt thereof is crenolanib besylate, crenolanib phosphate, crenolanib lactate, crenolanib hydrochloride, crenolanib citrate, crenolanib acetate, crenolanib toluenesulphonate, or crenolanib succinate.

6. A method for treating a subject suffering from leukemia comprising:
obtaining a sample from the subject;
determining from the subject sample that the subject has a deregulated FLT3 receptor or a constitutively active FLT3 receptor;
further determining that the subject is refractory to or has relapsed after administration of a prior tyrosine kinase inhibitor; and
administering to the subject in need of such treatment a therapeutically effective amount of crenolanib or a pharmaceutically acceptable salt thereof sufficient to treat the leukemia.

7. The method of claim 6, wherein at least one of:
the mutated or constitutively active FLT3 is at least one of FLT3-ITD; FLT3-TKD; an activating mutation in FLT3; a copy number gain or an amplification of the FLT3 gene; or a gene fusion comprising a fusion of FLT3 with another gene;
the mutation in the FLT3 gene or change in phenotype or genotype of FLT3 is a resistance conferring mutation selected from a missense mutation occurring in at least one of amino acid residues K429, A627, N676, A680, F691, Y693, G697, D698, N701, D835, N841, Y842, A848 present alone or in combination with a FLT3-ITD mutation; or
the resistance conferring FLT3 mutation was present before administration of the prior tyrosine kinase inhibitor or wherein the resistance conferring FLT3 mutation was acquired during or after administration of the prior tyrosine kinase inhibitor.

8. The method of claim 6, wherein the subject has been provided a prior tyrosine kinase inhibitor selected from midostaurin, sorafenib, gilteritinib, quizartinib, pexidartinib, FF-10101, CG-806, lestaurtinib, AG1295, AG1296, CEP-5214, CEP-7055, HM43239, pacritinib, MAX-40279, FYSYN, NMS-03592088, or TG02 citrate; or the subject has a FLT3 mutation that confers resistance to the prior tyrosine kinase inhibitor.

9. The method of claim 6, wherein the leukemia is selected from at least one of: Hodgkin's disease, a myeloma, acute promyelocytic leukemia (APL), chronic lymphocytic leukemia (CLL), chronic myeloid leukemia (CML), chronic neutrophilic leukemia (CNL); acute undifferentiated leukemia (AUL), anaplastic large-cell lymphoma (ALCL), prolymphocytic leukemia (PML); juvenile myelomonocytic leukemia (JMML); adult T-cell ALL, acute myeloid leukemia (AML), AML with trilineage myelodysplasia, myelodysplastic syndromes (MDS), myeloproliferative neoplasms (MPN), or multiple myeloma (MM).

* * * * *